US007014340B2

(12) United States Patent
Bettis

(10) Patent No.: US 7,014,340 B2
(45) Date of Patent: Mar. 21, 2006

(54) ILLUMINATION ASSEMBLY HAVING FLUID-TIGHT SEAL

(75) Inventor: Peter J. Bettis, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 54 days.

(21) Appl. No.: 10/393,841

(22) Filed: Mar. 21, 2003

(65) Prior Publication Data

US 2004/0184288 A1    Sep. 23, 2004

(51) Int. Cl.
*F21V 31/00*    (2006.01)

(52) U.S. Cl. .................. 362/267; 362/109; 600/199

(58) Field of Classification Search ................ 362/158, 362/255, 267, 572, 573; 313/318.08, 318.09, 313/318.1; 431/31; 600/199, 200, 245, 600/249

See application file for complete search history.

(56) References Cited

U.S. PATENT DOCUMENTS

| 3,137,804 | A | * | 6/1964 | Rubens ..................... 362/267 |
| 3,188,459 | A | * | 6/1965 | Bridwell ................... 362/227 |
| 3,499,226 | A | * | 3/1970 | Hopkins .................... 362/202 |
| 3,579,269 | A | * | 5/1971 | Ostensen ................... 362/158 |
| 3,592,199 | A |   | 7/1971 | Ostensen ................... 600/198 |
| 4,006,738 | A | * | 2/1977 | Moore et al. .............. 600/200 |
| 4,429,249 | A | * | 1/1984 | Tyler et al. ............... 313/113 |
| 4,672,263 | A | * | 6/1987 | Grahmann et al. .... 313/318.09 |
| 5,386,355 | A | * | 1/1995 | Acks ......................... 362/267 |
| 5,667,295 | A | * | 9/1997 | Tsui .......................... 362/267 |
| 5,685,638 | A | * | 11/1997 | Huang ....................... 362/267 |
| 6,099,147 | A | * | 8/2000 | Ziegenfuss ................ 362/158 |
| 6,277,068 | B1 |  | 8/2001 | Wojnowicz et al. ........ 600/199 |

* cited by examiner

*Primary Examiner*—Alan Cariaso
(74) *Attorney, Agent, or Firm*—Wall Marjama & Bilinski LLP

(57) ABSTRACT

An illumination assembly for a medical diagnostic instrument, includes an open ended lamp housing, an incandescent lamp disposed within the housing. A peripheral sealing member is disposed in intimate contact with the exterior surface of the lamp envelope such that initial energization of said lamp causes the sealing member to create a substantial fluid-tight seal with the lamp to protect the interior of the housing, including the electrical contacts of the assembly.

11 Claims, 4 Drawing Sheets

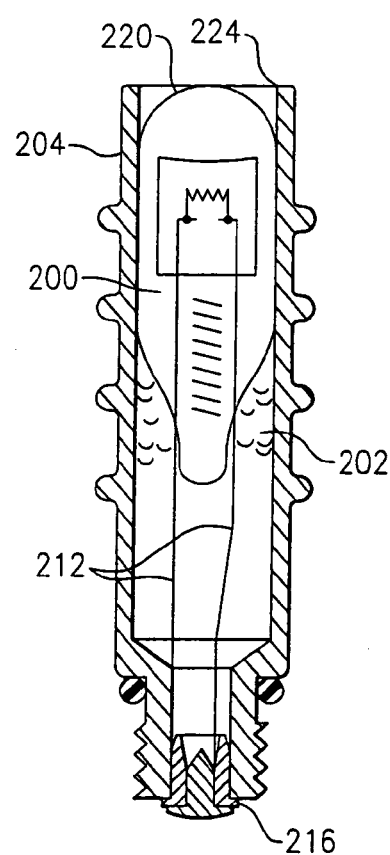
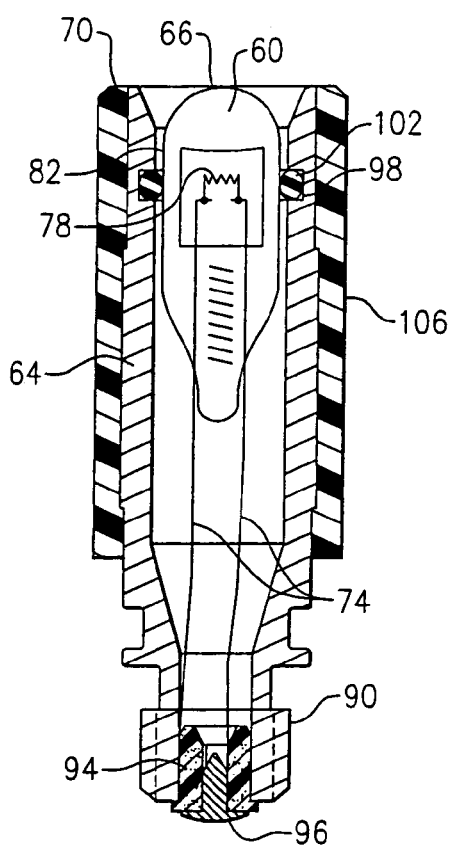
FIG.1
Prior Art
FIG.4
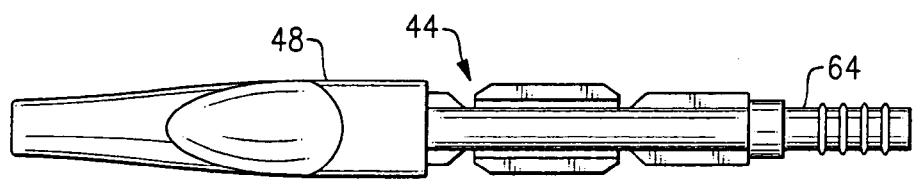
FIG.3

ILLUMINATION ASSEMBLY HAVING FLUID-TIGHT SEAL

FIELD OF THE INVENTION

This invention relates to the field of illumination devices and in particular to the development of a fluid-tight seal in a lamp housing.

BACKGROUND OF THE INVENTION

There are known illumination assemblies in the medical diagnostic field, such as the 78010 illuminator assembly manufactured by Welch Allyn Inc., in which a miniature halogen or other miniature incandescent lamp is retained within the confines of a lamp housing. The lamp housing is threaded or otherwise disposed into the distal end of a assembly receptacle or assemblage containing a number of electrical contacts and having a proximal end with a strain relief and a cord containing electrical connectors extending to a power supply, such as a transformer. The assembly receptacle, including the lamp housing, can be implanted into the confines of a handle of a disposable vaginal speculum, such as those described in U.S. Pat. No. 3,176,047, the speculum being equipped with a light conducting end that is configured in order to direct light from the miniature contained halogen bulb to permit conduction of pelvic examinations.

During use in the vaginal speculum, the above described illumination assembly is subsequently exposed to fluids, requiring that the lamp be cleaned and sterilized following use or that the life of the lamp is shortened prematurely due to the presence of fluids entering the housing and corrupting the electrical leads and lamp contacts. To date, there has not been provided an effective technique for providing a fluid-tight seal for a lamp in an illumination assembly such as those described above.

Referring to FIG. 1, and in the assembly of a typical lamp housing, cement, epoxy or other suitable applied adhesive 202 is added into secure the position of the miniature incandescent lamp 200 within the lamp housing 204 as the electrical leads 212 of the lamp are drawn through the bottom of the lamp housing for attachment to the remainder of the illuminator assemblage and more particularly to a contact 216. It is essential during this process that the distal end 220 of the lamp 200 be maintained properly at the distal end 224 of the lamp housing 200. Without the adhesive 202, the lamp 200 would not hold its desired position within the housing when the leads 212 are drawn to the contact 216.

The preceding manufacturing process fails to provide a fluid-tight seal for the lamp housing in that moisture migrates through microfissures that are formed in the adhesive and as readily apparent fails to provide any form of protection for the lamp itself as fluids can easily permeate the boundary between the envelope of the bulb and the interior of the housing.

SUMMARY OF THE INVENTION

It is therefore a primary object of the present invention to overcome the above-noted deficiencies of the prior art.

It is therefore another primary object of the present invention to provide an illumination assembly for a medical diagnostic or other instrument that is exposed to fluidic environment(s) capable of shortening the effective life of such instruments.

Therefore and according to a preferred aspect of the invention, there is provided an illumination assembly comprising a miniature incandescent lamp fitted within a housing, and an elastomeric sealing member disposed between an inner surface of the housing and the outer surface of the incandescent lamp, wherein the sealing member is placed in intimate contact with the lamp such that the sealing member fuses to said lamp while maintain a permanent substantially fluid-tight seal.

Preferably, the sealing member is made from a similar material as the glass envelope of the lamp such that the fusion process produces a coalescence between the envelope of the lamp and the exterior surface of the sealing member, thereby resulting in a highly effective seal without destroying the integrity of the sealing member or interfering with the illumination capacity of the miniature incandescent lamp.

Preferably, the sealing member is a silicon O-ring that is fitted within an peripheral inner slot provided within the lamp housing, the seal being initiated the first time the lamp is energized. Preferably, the ring is placed into compressive contact with the lamp prior to energization, the slot providing an interference fit with the housed bulb.

According to another preferred aspect of the present invention, there is provide a method of effectively sealing a lamp within a lamp housing, the method including the steps of:

disposing a miniature incandescent lamp within a lamp housing;

placing the exterior surface of a sealing member disposed in said lamp housing into intimate contact with the envelope of a miniature incandescent lamp; wherein energizing said lamp creates a substantially fluid tight seal between said lamp and the sealing member.

An advantage of the present invention is that the formation of a fluid tight seal within the lamp housing protects the interior of the housing from damage that may occur environmentally during use of the illuminator in a medical diagnostic instrument. As a result, the life of the instrument, including that of the lamp, is effectively increased.

Yet another advantage is that the created seal allows the illuminator assembly to be soaked for cleaning and sterilization purposes, a feature heretofore not possible with these assemblies.

These and other objects, features and advantages will become readily apparent from the following Detailed Description which should be read in conjunction with the accompanying drawings.

BRIEF DESCRIPTION OF THE DRAWINGS

FIG. 1 is a partial side sectional view of a lamp housing for an illuminator assembly made in accordance with the prior art;

FIG. 3 is a side view of a portion of the illuminator assembly including a lamp housing made in accordance with the present invention;

FIG. 4 is partial side sectioned view of the lamp housing of FIG. 3;

DETAILED DESCRIPTION

The following description relates to a specific illumination assembly for use in a vaginal speculum. It will be readily apparent to one of sufficient skill in the field, however, that the present invention can be utilized in literally any medical or other instrument that includes an illumination assembly and is exposed to a fluidic environment.

Figure 2:
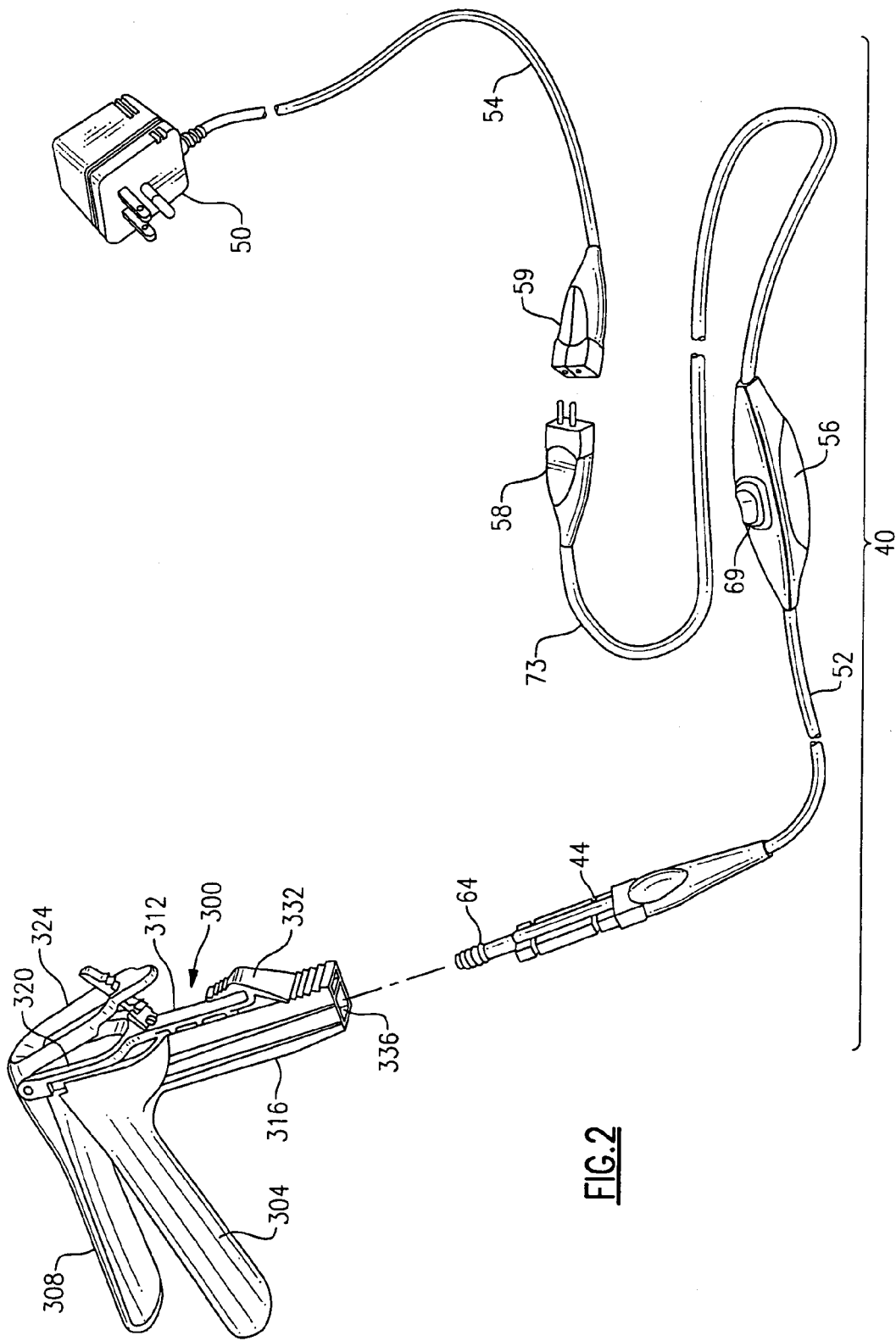
FIG. 2 is a top perspective view of a vaginal speculum using the illuminator assembly of the present invention.

Referring to FIG. 2, and as a point of background, an illuminator assembly 40 in accordance with the present invention is shown as used with a disposable vaginal speculum 300. In brief, the disposable vaginal speculum 300 includes three main interconnected components; namely, a fixed blade member 304, a movable blade member 308 and a slide member 312. Each of the above components are made from a clear, tough plastic material, such as acrylic or polystyrene, in which the fixed blade member 304 includes a trough shaped blade and a hollow leg 316. The slide member 312 includes a forked upper end 320 that receives the movable blade member 308 which is pivotally attached thereto, including a lever portion 324, the slide member further including a lower tongue 332 having ratchet teeth that engage with corresponding teeth provided on the rear side of the hollow leg 316 of the fixed blade member 304 of the speculum 300 to provide adjustment therebetween. Additional details concerning the herein described disposable vaginal speculum can be found in U.S. Pat. No. 3,716,047, the entire contents of which are herein incorporated by reference.

The hollow leg 316 of the fixed blade member 304 of the disposable vaginal speculum 300 includes a slot 336 that is sized for receiving an illuminator assembly as well as an interior curved light bar (not shown) that receives the light from a miniature incandescent lamp contained in the illuminator assembly and directs it along a longitudinal axis of the fixed blade member 304. Details concerning the curved light bar can also be found in the previously incorporated U.S. Pat. No. 3,716,047.

Figure 5:
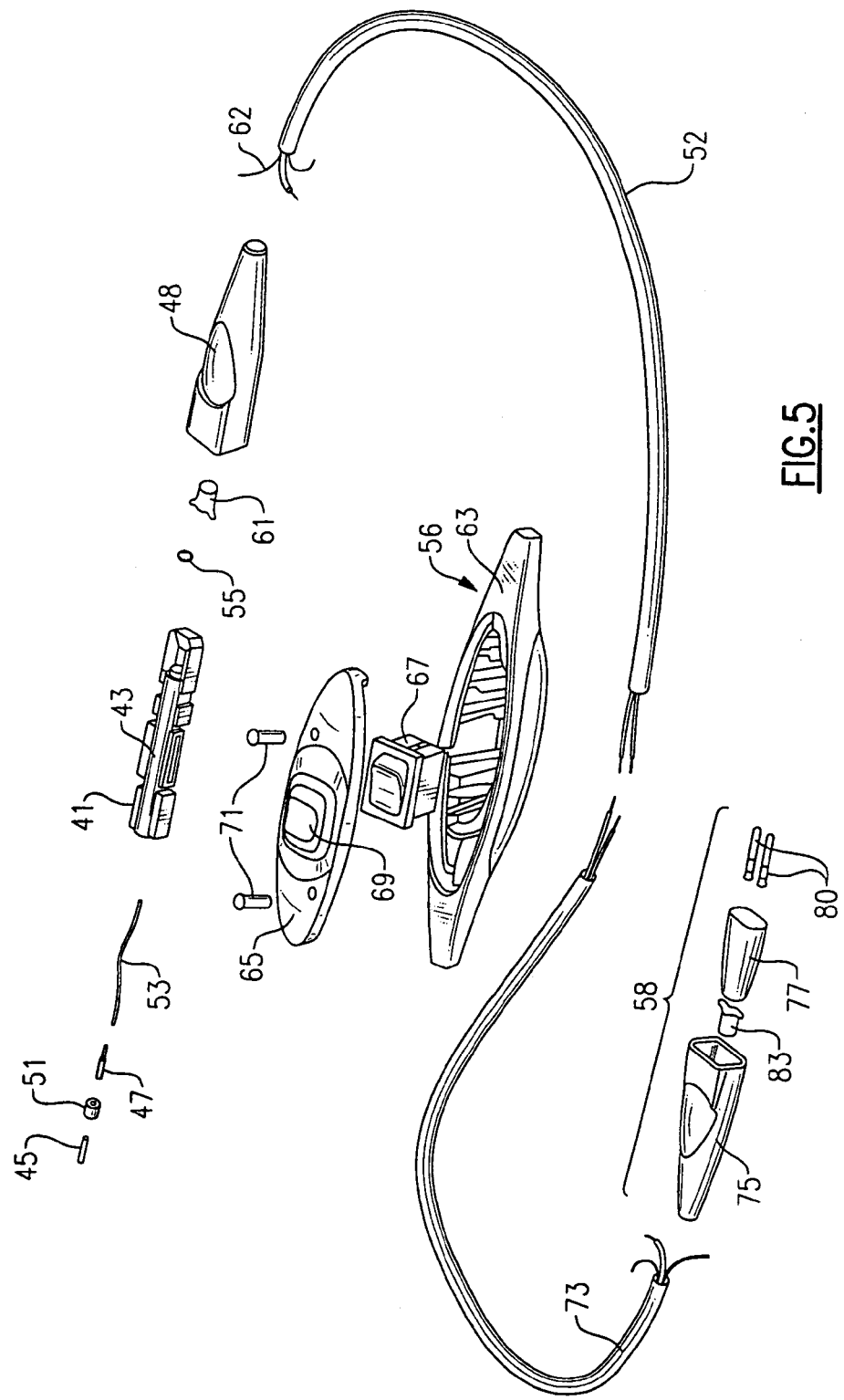
FIG. 5 is an exploded view of the illuminator assembly of FIG. 3, including an in-line illuminator switch assembly.

Referring to FIGS. 2 and 3 and 5, the illuminator assembly 40 includes an illuminator assemblage 44 in the form of a plastic outer section 41 having a molded cavity sized for fitting an elongate metal tube 43 therein. The distal end of the assemblage 44 includes a contact pin 45 that is fitted into a contact socket 47 surrounded by an insulator 51, each of which are fitted into the distal end of the contained metal tube 43. A lead wire 53 attached to the contact socket 47 extends through the interior of the metal tube 43 and a wing band 55 and a wire splice 61 are provided at the proximal end thereof, retaining the end of the extending lead wire and guiding same to the interior of a grippable strain relief 48 to interconnect same with a set of electrical conductors. The grippable strain relief 48 includes a distal end having a cavity sized for engaging the proximal end of the plastic section 41, thereby forming the assemblage 44.

An insulated electrical cable 52 is tethered to the assemblage at the grippable strain relief 48 at one end, the cable containing the appropriate electrical conductors 62 and to an in-line illumination switch assembly 56 at its opposing end. The in-line illumination switch assembly 56 includes an elongated housing 63 having a cover 65. The housing defines an enclosure having a rocker switch 67 interposed in the center thereof. The cover 65 includes an opening retaining a flexible boot 69, the boot being made from santoprene or an equivalent material, covering the switch 67, the cover being attached to the top of the housing by a set of fasteners 71. Another electrical cable 73 extends from the opposite side of the in-line illuminator switch assembly 56, this cable including a proximal end terminating in a plug 58 having a strain relief 75 and a pre-molded body including a set of male connector pins 80 for engaging a corresponding plug 59 extending to a power supply, such as a transformer 50 along a corresponding electrical cable 54. A wing band 83 collects the ends of the electrical conductors 62 within the cable for electrical interconnection to the connector pins 80. Preferably, the in-line illumination switch assembly 56 includes strain reliefs on either side for the attached electrical cables 52, 73.

Still referring to FIGS. 2 and 3, a lamp housing 64, not shown in FIG. 5, is retained by the illuminator assemblage 44 that is releasably mounted by screw threads to permit replacement thereof at the distal end of the assemblage.

Referring to FIG. 4, the lamp housing 64 of the present invention is detailed. The miniature incandescent lamp 60, such as a Model 07800 6-volt halogen lamp manufactured by Welch Allyn, Inc., is disposed within a cylindrical open-ended housing 64, made from nickel-plated brass, the distal end 66 of the lamp being arranged to be coplanar with the distal end 70 of the housing. It should be point out that the lamp housing can alternatively be made from other suitable electrically conductive materials, such as, for example, stainless steel. A set of lamp leads 74 extend from the lamp filament 78 through the bottom of the glass bulb envelope 82. The lamp leads 74 extend through the entire length of the lamp housing 64 and terminate at an electrical contact 86, this contact being added to the proximal end 90 of the lamp housing by an insulator 94.

An elastomeric sealing member, in this instance, an O-ring 98, is disposed in a circumferential slot 102 that is formed in the interior of the open ended lamp housing 64. The O-ring 98 according to this embodiment is made from untreated silicone wherein it is desirable to provide a sealing member made from a material as similar as possible to that of the glass bulb envelope 82. As noted, the O-ring 98 is elastomeric. According to the present embodiment, the O-ring is approximately on or about 70 Durometer, Shore A. The O-ring 98 engages the exterior of the glass bulb envelope 82 and forms an interference fit therewith, the O-ring being disposed substantially close to the distal end 70 of the housing 64. A sleeve 106 made from a heat-resistive material, such as ultem or other suitable material, covers the exterior of the lamp housing 64 to prevent injury or burns when it is touched during or immediately after lamp energization.

Figure 6:
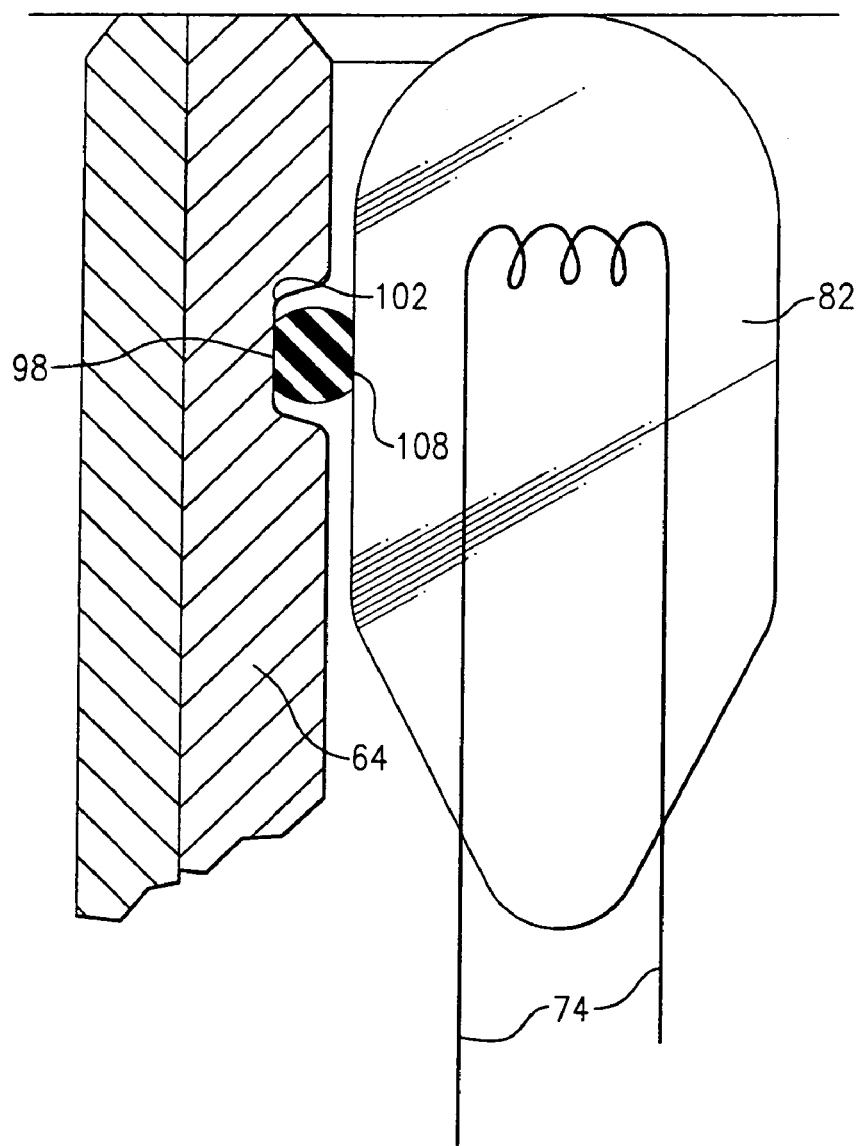
FIG. 6 is an enlarged view of the sealing portion of FIG. 4 taken between the lamp and the sealing member.

The O-ring 98 extends only partially into the circumferential slot 102 and is therefore placed into compressive contact with the exterior of the glass bulb envelope 82. Referring to FIG. 6 and upon energization of the lamp 60, the exterior surface of the O-ring 98 exceeds its transition temperature due to the heat generated by the lamp causing the incident exterior contacting surface of the O-ring 98 to coalesce with that of the glass bulb envelope 82, creating a bond 108 and therefore a highly effective peripheral fluid-tight static seal which remains even after the lamp has been deenergized.

In the manufacturing process and referring most particularly to FIG. 4, the lamp 60 is initially placed into the open-ended lamp housing 64, similarly to that of FIG. 1. Cement or other epoxy (not shown) can be used, if desired, to properly maintain the lamp's datum to the upper surface of the illumination assembly 40, though the compressive contact of the O-ring 98 will accomplish same to permit the lamp leads 74 to be properly routed and attached to the contact 86 without displacing the lamp out of position.

Following the interconnection of the lamp 60 to the contact 86 of the illuminator assembly 40, FIG. 2, the lamp can be initially energized to create the fluid-tight seal prior to use or the seal can be created during first use of the assembly. The seal created is permanent due to the coalescence and primarily due to ionic chemical bonds that are produced between the sealing member 98 and the lamp bulb envelope.

Once assembled, the miniature incandescent lamp 60 can be energized selectively by means of the in-line switch assembly 56. Electrical contact is established between the contact 86 of the lamp 60 and the contact pin 45 extending through lead wire 53 to the electrical conductors 62 in the electrical cable 52 extending to cable 73 and ultimately to the transformer 50. The in-line illumination switch assembly, through boot 69 enabling rocker switch 57, energizes the lamp by completing or closing the above connection selectively, wherein the boot provides a seal to the interior of the assembly housing 63.

In use, the illuminator assemblage 44 is placed within the slot 336 of the fixed blade member 204 of the disposable vaginal speculum 200, in the manner depicted according to FIG. 2 for the examination of a patient. Due to the fluid-tight seal formed between the lamp 60 and the lamp housing 64, the effective life of the lamp and the illuminator assembly 40 is effectively increased.

PARTS LIST FOR FIGS. 1–6

40 illuminator assembly
41 plastic portion
43 metal body
44 illuminator assemblage
45 contact pin
47 contact socket
48 grippable-strain relief
50 transformer
51 insulator
52 electrical cable
53 lead wire
54 electrical cable
55 wing band
56 illuminator switch assembly
58 plug
59 plug
60 miniature incandescent lamp
61 wire splice
62 electrical conductors
63 assembly housing
64 lamp housing
65 cover
66 distal end—lamp
67 rocker switch
69 flexible boot
70 distal end—lamp housing
71 fasteners
73 cable
74 lamp leads
75 molded body
78 filament—lamp
80 male connector pins
82 lamp envelope
83 wire band
86 contact
90 proximal end
94 insulator
98 O-ring
102 circumferential slot
106 sleeve
108 bond
200 miniature incandescent lamp
202 adhesive
204 housing
212 electrical leads
216 contact
220 distal end—lamp
224 distal end—housing
300 disposable vaginal speculum
304 fixed blade member
308 movable blade member
312 slide member
316 hollow leg
320 forked upper end
324 lever portion
332 lower tongue
336 slot While the present invention has been particularly shown and described with reference to the preferred mode as illustrated in the drawings, it will be understood by one skilled in the art that various changes in detail may be effected therein without departing from the spirit and scope of the invention as defined by the claims.

We claim:

1. An illumination assembly for a medical diagnostic instrument, said assembly including:
    an open-ended lamp housing made from an electrically conductive material,
    an incandescent lamp disposed within one end of said open-ended lamp housing, and
    an O-ring disposed in intimate contact with said lamp, said O-ring being made from a material which has a transition temperature that is lower than that of an energized lamp, said O-ring being interposed between said electrically conductive lamp housing and the envelope of said lamp such that initial energization of said lamp causes said O-ring to chemically bond with said envelope and create a permanent circumferential fluid-tight seal with said lamp to prevent fluids from entering the confines of said lamp housing.

2. An assembly as recited in claim 1, wherein said O-ring is made from silicone.

3. An assembly as recited in claim 1, including a heat-resistive sleeve for covering the exterior of said open-ended lamp housing.

4. An assembly as recited in claim 1, wherein the interior surface of said lamp housing includes an inner slot for retaining a peripheral portion of said O-ring.

5. A method of effectively and permanently sealing a lamp within an open-ended lamp housing, the method including the steps of:
    disposing a miniature incandescent lamp into one end of an open-ended lamp housing, said lamp housing being made from an electrically conductive material;
    placing the exterior surface of an O-ring disposed in said lamp housing between an interior surface of said electrically conductive lamp housing and said lamp and into compressive contact with the envelope of said miniature incandescent lamp, said O-ring being made from a material which has a transition temperature lower than that of an energized lamp; wherein
    energizing said lamp creates a permanent substantially fluid tight seal between said lamp and said O-ring wherein said O-ring chemically interacts and coalesces with said lamp envelope.

6. A method as recited in claim 5, wherein said O-ring is made from a material that is similar to that of the envelope of the incandescent bulb.

7. A method as recited in claim 6, wherein said O-ring is made from silicone.

8. A method as recited in claim 5, wherein the interior surface of said electrically conductive lamp housing includes at least one interior feature for retaining said O-ring.

9. A method as recited in claim 5, wherein said lamp housing is part of an illumination assembly for a hand-held medical instrument.

10. A method as recited in claim 5, wherein said O-ring is placed into said lamp housing prior to disposing said incandescent lamp therein.

11. A method for assembling an illumination assembly, said method comprising the steps of:

placing an annular sealing member within a circumferential slot of an open-ended lamp housing;

positioning a miniature incandescent lamp within said open-ended lamp housing such that the envelope of said lamp is in put into intimate compressive contact with the annular sealing member, said annular sealing member being made from a material which is similar to that of said lamp envelope and having a transition temperature that is lower than that of the exterior of an energized lamp; and energizing said lamp thereby fusing said sealing member and said lamp housing together and creating a permanent fluid-tight seal between said lamp and said lamp housing wherein said energizing step fixedly positions said lamp in said illumination assembly.

* * * * *

UNITED STATES PATENT AND TRADEMARK OFFICE
CERTIFICATE OF CORRECTION

| | | |
|---|---|---|
| PATENT NO. | : 7,014,340 B2 | |
| APPLICATION NO. | : 10/393841 | |
| DATED | : March 21, 2006 | |
| INVENTOR(S) | : Peter J. Bettis | |

It is certified that error appears in the above-identified patent and that said Letters Patent is hereby corrected as shown below:

Column 8, Line 5 the phrase "in put" should read --put--.

Signed and Sealed this

Twenty-ninth Day of August, 2006

JON W. DUDAS
*Director of the United States Patent and Trademark Office*